United States Patent [19]
Kondou et al.

[11] Patent Number: 5,221,893
[45] Date of Patent: Jun. 22, 1993

[54] METHOD AND DEVICE FOR DIAGNOSIS OF PAINT FILM DETERIORATION

[75] Inventors: Takeshi Kondou, Gifu; Sumio Yamamoto, Yokohama, both of Japan

[73] Assignee: Kabushiki Kaisha Toshiba, Kanagawa, Japan

[21] Appl. No.: 840,668

[22] Filed: Feb. 20, 1992

Related U.S. Application Data

[62] Division of Ser. No. 682,918, Apr. 9, 1991, abandoned.

[51] Int. Cl.⁵ .................... G01N 27/02; G01R 27/16
[52] U.S. Cl. .................... 324/71.2; 324/693; 324/700; 324/707; 324/721; 427/8
[58] Field of Search ............... 324/693, 699, 700, 707, 324/713, 715, 716, 718, 720, 721, 71.1, 71.2, 72.5; 427/8, 9, 10

[56] References Cited

U.S. PATENT DOCUMENTS

| | | | |
|---|---|---|---|
| 3,416,078 | 12/1968 | Boncuk et al. | 324/716 |
| 3,559,053 | 1/1971 | Tagg | 324/713 |
| 3,936,738 | 2/1976 | Maltby | 324/71.1 |
| 4,338,563 | 7/1982 | Rhoades et al. | 324/721 X |
| 4,806,849 | 2/1989 | Kihira et al. | 324/718 X |
| 4,962,360 | 10/1990 | Homma et al. | 324/700 |

FOREIGN PATENT DOCUMENTS

| | | |
|---|---|---|
| 59-34143 | 2/1984 | Japan. |
| 62-102148 | 5/1987 | Japan. |
| 62-229056 | 10/1987 | Japan. |

OTHER PUBLICATIONS

Tooru Tsuru, "AC Impedance Method and Its Application to Corrosion and Corrosion Prevention," Rust Prevention Control, vol. 11, 1986, pp. 13-19.

Primary Examiner—Jack B. Harvey
Assistant Examiner—Glenn Brown
Attorney, Agent, or Firm—Limbach & Limbach

[57] ABSTRACT

In a method of diagnosing deterioration of a paint film, a probe is applied to the surface of a paint film. A voltage having a predetermined waveform is applied by a preamplifier across the probe and a base metal on which the paint film is formed. A current flowing through the paint film is measured by the preamplifier. An analog signal indicative of a measured current value is converted to a corresponding digital signal by an analog-to-digital converter. A personal computer operates to analyze the digital signal in accordance with a predetermined analyzing procedure so that the degree of deterioration of the paint film is determined. The resultant determination is displayed on the display.

5 Claims, 5 Drawing Sheets

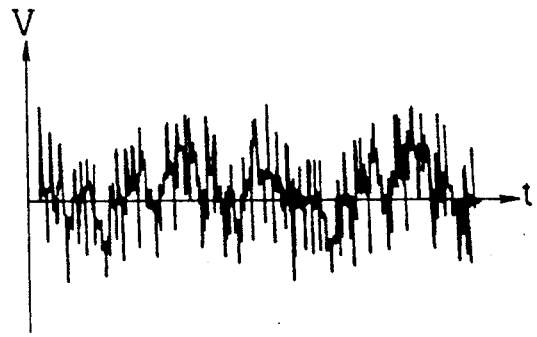

(1) Prediction of degree of deterioration

The paint film deterioration is classified into the following ranks A to C:

Rank A: The paint film is in a sound condition though reduced gloss and choking are perceived to some extent.

Rank B: Corrosion of the base metal is in progress though rust cannot be visually perceived.

Rank C: Rust is conspicuous and rust prevention effect of the paint film has been reduced.

"Deterioration of the paint film is presumed to be in rank B as the result of the present measurement."

(2) Prediction of time of repainting

The time of repainting refers to a stage in which the base metal has begun to develop symptoms of rust.
When the repainting is carried out at this stage, a most economic corrosion preventive paint can be obtained without a serious rusting on the base metal under the paint film.

The time of repainting can be predicted as follows as the result of the present measurement:

"It would be better to consider repainting within 0.4 years since a symptom of deterioration can be perceived."

METHOD AND DEVICE FOR DIAGNOSIS OF PAINT FILM DETERIORATION

This is a divisional application of co-pending application Ser. No. 07/682,918 filed on Apr. 9, 1991, now abandoned.

BACKGROUND OF THE INVENTION

This invention relates generally to a method and device for determining the degree of aged deterioration of a paint film formed on the surface of a metal member of an equipment, and more particularly to such a paint film deterioration diagnosing method and device wherein the degree of deterioration of the paint film is determined from an impedance of the paint film.

A paint film is usually formed on the outer surface of an equipment installed outdoors, for example, transformers or switchboards for the purposes of corrosion prevention, appearance improvement and the like. It is known in the art that the paint film formed on the outer surface of the equipment is deteriorated with time at different speeds depending upon environment of the equipment. When the paint film is left deteriorated, corrosion of a base metal covered by the paint film finally causes flaking of the paint film and occurrence of rust. The equipment needs to be repainted at an appropriate time for maintenance thereof so that a new paint film is formed on the outer surface of the equipment. When repainting is carried out too early, it results in wasting the cost therefor. When repainting is carried out too late, an economic burden is increased since repair of the corroded base metal takes much time. Thus, when an opportunity for repainting is missed, a bad influence is exerted on the maintenance of the equipment. Conventionally, in the above-mentioned equipments, the degree of deterioration of the paint film is periodically diagnosed so that an appropriate opportunity for repainting is determined.

It is desirable that the result of the above-mentioned diagnosis should have as much objectivity as possible or an appropriate determination should always be made no matter who carries out the diagnosis. In consideration of this point, the prior art has provided the following method of diagnosing the deterioration of the paint film. A large number of sample photographs are previously prepared which show different stages of deterioration with respect to various conditions of deterioration such as peeling, cracking, blistering, rusting and the like. The paint film to be actually diagnosed is compared with the sample photographs by a workman engaged in the diagnosis. The workman understands what stages of the sample photographs the condition of the paint film to be diagnosed corresponds to with respect to various conditions of deterioration and further, assigns predetermined scores with respect to various conditions and degrees of deterioration. The scores are sequentially added. When the value obtained from addition of scores reaches a predetermined value, it is determined by the workman that repainting or repair and repainting should be carried out.

The prior art has provided another method of diagnosing the paint film deterioration, which method is somewhat in advance of the above-described one. This method makes use of an impedance of the paint film varied depending upon the degree of deterioration. This method is disclosed in Japanese Laid-open (kokai) Patent Application No. 62-102148 (1987) filed by the assignee of the present application, for example. An actually employed diagnosis procedure in accordance with this method is summarized as follows. An impedance measurement device is brought into a place where the equipment as an object to be diagnosed is installed. A probe is applied to the surface of the paint film and voltages at various frequencies are applied across the probe and a base metal on which the paint film is formed. The paint film impedance values measured based on the currents flowing as the result of voltage application are read by the workman to be written down. The resistive and capacitive impedance values written down with respect to various frequencies are compared with a previously prepared list for determining what columns in the list the impedance values correspond to, thereby determining the degree of the paint film deterioration. The frequency for measuring the paint film impedance is usually 200 Hz, 500 Hz or 1 KHz.

In the former method, however, the determination to which of the sample photographs the actual degree of the paint film deterioration corresponds tends to be influenced by the subjectivity of the workman engaged in the diagnosis. Thus, this method cannot warrant that every workman can always carry out an appropriate diagnosis. Accordingly, the result of the diagnosis is not likely to be highly esteemed and therefore, repainting or repair of the equipment with painting is not carried out at an appropriate time. Furthermore, this method necessitates for the workman to compare the actual paint film with a number of sample photographs and to add the scores. These works are troublesome and miscalculations can occur in adding the scores.

On the other hand, in the latter method in which the impedance of the paint film is measured, there is a possibility that readings of measured values may be influenced by the operator's subjectivity. Additionally, it is troublesome to compare the measured values with criterion for evaluation.

SUMMARY OF THE INVENTION

Therefore, an object of the present invention is to provide an improved method and device for diagnosis of paint film deterioration wherein the diagnosis of the paint film deterioration can be prevented from being influenced by the subjectivity of a person engaged in the diagnosis so that an appropriate result of diagnosis can be obtained and the diagnosing works can be carried out with ease and accuracy.

The present invention provides a method of diagnosing deterioration of a paint film comprising applying a probe to the surface of a paint film, applying voltage having a predetermined waveform, across the probe and a base metal on which the paint film is formed, measuring a current flowing into the probe through the paint film when the voltage is applied across the probe and the base metal, converting an analog signal indicative of the measured current to a corresponding digital signal, analyzing the digital signal by a computer in accordance with a predetermined analyzing procedure so that a degree of deterioration of the paint film is determined.

In accordance with the above-described method, when a voltage is applied by the voltage applying means across the base metal and the probe, a current is caused to flow into the probe through the paint film. The current flowing into the probe is measured by the current measuring means. An analog signal obtained by the current measuring means is converted to a corresponding digital signal by the analog-to-digital conversion means and the digital signal is inputted to a computer. It is known that the magnitude and phase of a current flowing into a paint film, that is, an impedance of the paint film has a correlation with the degree of deterioration of the paint film. The degree of deterioration of the paint film is determined by the computer from the digital signal outputted by the analog-to-digital conversion means in accordance with an analysis procedure which is previously determined in consideration of conditions of the applied voltage, frequency and the like and the above-mentioned correlation. The result of determination is outputted by the output means. What is necessary for the workman to do is to apply the probe on the surface of the paint film to be diagnosed and to operate the computer so that the degree of deterioration of the paint film is determined. Consequently, an objective determination result can be obtained.

The present invention also provides a method and means of diagnosing a degree of deterioration of a paint film based on an impedance measured by applying a probe to the surface of the paint film and applying voltage across the probe and a base metal on which the paint film is formed, the method comprising steps of providing a microcomputer with an operational program representative of a functional expression corresponding to an orthogonal graph having an axis representative of the impedance and an axis representative of an elapsed service time period in the year, inputting to the microcomputer data of an initial impedance of the paint film measured at the time of formation of the paint film, the measured impedance, an elapsed time period until the measurement of the paint film, and a predetermined life-end-point impedance of the paint film, performing an operation for obtaining an equation representative of a line passing through the initial impedance and the measured impedance, performing an operation for obtaining a life end point of the paint film by substituting the life-duration impedance into the equation representative of the line passing through the initial impedance and the measured impedance in the microcomputer, obtaining a remaining life-duration of the paint film from the time of measurement of the impedance of the paint film to the life end point in the microcomputer, and displaying the obtained remaining life-duration of the paint film on a display.

The inventors have found that a paint film impedance is conspicuously varied in a low frequency range with time and that logarithms of impedance values are linearly reduced with time. Accordingly, the degree of deterioration of the paint film can be accurately determined from the initial impedance value, the number of elapsing years after formation of the paint film and the measured impedance value when an initial impedance with respect to the kinds of paints of the paint film is previously obtained from, for example, experiments in consideration of these relations found by the inventors. Consequently, an appropriate time for repainting can be accurately determined.

The present invention also provides a method of diagnosing deterioration of a paint film, comprising applying a probe to the surface of a paint film and applying a voltage having a predetermined waveform across the probe and a base metal on which the paint film is formed, measuring a current flowing into the probe through the paint film, writing data of the measured current into a portable storage medium, attaching the storage medium to a determination device so that the written data of the measured current is read out from the storage medium, and transferring the read-out data to determination means so that the degree of deterioration of the paint film is determined.

In accordance with the above-described method, even when the electrical equipments to be diagnosed, for example, transformers, are located far away, the workman goes round to the locations of the equipments with a current measuring device carried in order to measure the current flowing into the probe. Only the storage medium is brought into central maintenance facilities, where the storage medium is attached to the determination device. Thus, the determination of deterioration of the paint film can be carried out collectively with respect to a large number of electrical equipments. Consequently, the diagnosis of the paint film deterioration can be controlled with ease.

Other objects of the present invention will become obvious upon understanding of the illustrative embodiment about to be described or will be indicated in the appended claims. Various advantages not referred to herein will occur to one skilled in the art upon employment of the invention in practice.

BRIEF DESCRIPTION OF THE DRAWINGS

FIG. 3 illustrates an example of waveform of a voltage applied to the paint film;

FIG. 4 shows an example of the diagnosis result on display;

DESCRIPTION OF THE PREFERRED EMBODIMENT

Figure 1:
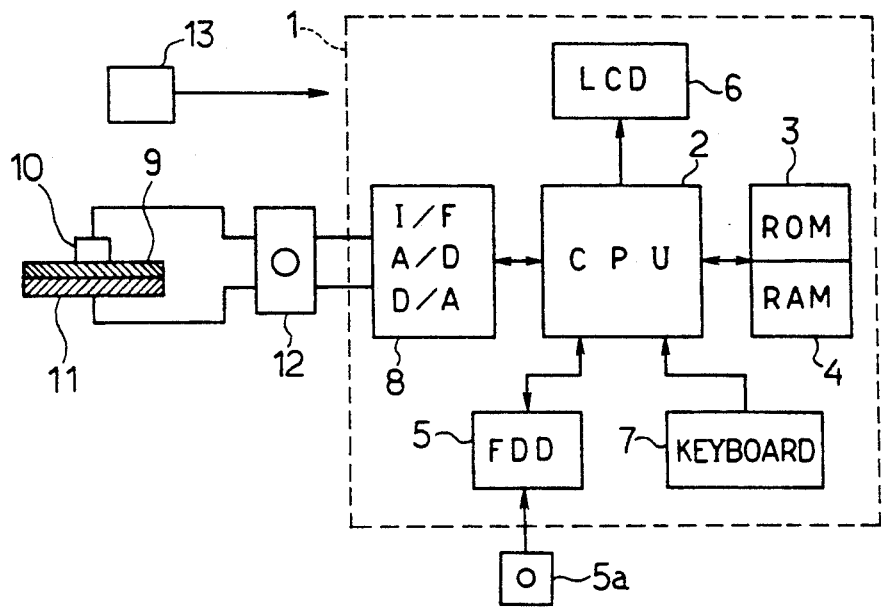
FIG. 1 is a block diagram of a paint film deterioration diagnosis device of an embodiment in accordance with the present invention.

An embodiment of the present invention will be described with reference to the accompanying drawings. Reference numeral 1 designates a so-called lap-top type personal computer. A casing (not shown) thereof encloses a central processing unit (CPU) 2, a read only memory (ROM) 3, a random access memory (RAM) 4, a floppy disc drive (FDD) 5 and the like. The personal computer 1 includes a liquid crystal display 6 and a keyboard 7. An interface (I/F) board 8 with analog-to-digital and digital-to-analog conversion functions is inserted in an expansion slot of the personal computer 1.

A probe 10 is applied to a paint film 9 to be diagnosed with respect to deterioration thereof. Various types of such probes are well known. See Japanese Laid-open (kokai) Patent Application No. 61-108954, for example. Basically, the probe 10 comprises a container containing spongy electrodes impregnated with a conductive gel and a permanent magnet provided along the peripheral edge of an opening of the container. The spongy electrodes of the probe 10 are closely adhered to the surface of the paint film 9 by an attractive force incurred between the permanent magnet and a base metal 11 on which the paint film 9 is formed. A lead wire extended from the probe 10 and another lead wire connected to the base metal 11 are connected to a preamplifier 12 so that a voltage signal in accordance with a current flowing into the probe 12 through the paint film 9 when voltage is applied across the probe 10 and the base metal 11 is supplied to the I/F board 8 of the personal computer 1. The preamplifier 12 thus serves as current measuring means for measuring a current flowing into the probe 10 across the paint film 9. This current measurement corresponds to measuring an impedance of the paint film 9. The preamplifier 12 is designed to switch its measurement ranges depending upon degree of deterioration of the paint film 9. In the embodiment, the preamplifier 12 covers a measurable current range between 0.01 $\mu$A and 10 $\mu$A, the range corresponding to an impedance range between 0.1 M$\Omega$ and 100 M$\Omega$.

A procedure for diagnosing the paint film 9 with the deterioration diagnosis device thus arranged will now be described with functions of the personal computer 1.

First, the personal computer 1, the preamplifier 12 and the probe 10 are brought into a place where the diagnosis of deterioration is carried out. The probe 10 is applied to the surface of the paint film 9 and then connected to the preamplifier 12 which is further connected to the personal computer 1, as shown in FIG. 1. A floppy disc 5a storing data of a measurement program is inserted into FDD 5 so that the personal computer 1 inputs the data from the floppy disc 5a and executes the measurement program. As the result of execution of the measurement program, a voltage is applied across the probe 10 and the base metal 11 and a current flowing into the paint film 9 at the time of the voltage application is detected by the preamplifier 12, which then, supplies the I/F board 8 of the personal computer 1 with a voltage signal indicative of the detected current. The analog voltage signal supplied to the I/F board 8 is converted to a corresponding digital signal by the A/D conversion function thereof. The digital signal produced from the I/F board 8, that is, data of the measured impedance is written into the floppy disc 5a in FDD 5 under the control of CPU 2. Such a paint film impedance measurement as described above is carried out with respect to a plurality of measurement portions on the paint film surface. Measurement data of the temperature T of the paint film 9 or the equipment measured by temperature measuring means 13 at the time of measurement of the paint film impedance, the thickness of the paint film 9, the area of the probe 10 in contact with the paint film surface and the like is inputted at the keyboard 7 of the personal computer 1 along with measurement of the paint film impedance, which data being registered in the floppy disc 5a.

A waveform of the voltage applied across the probe 10 and the base metal 11 is generated and composed by the D/A conversion function of the I/F board 8 based on digital data previously stored in the floppy disc 5a. The I/F board 8 thus serves as voltage applying means for applying a voltage with a predetermined waveform across the probe 10 and the base metal 11 covered by the paint film 9. In the embodiment, the frequency of the applied voltage ranges from 0.01 Hz to 1 Hz and power spectrum P is between $P=1/\sqrt{f}$ and $P=1/f^2$.

Figure 2:
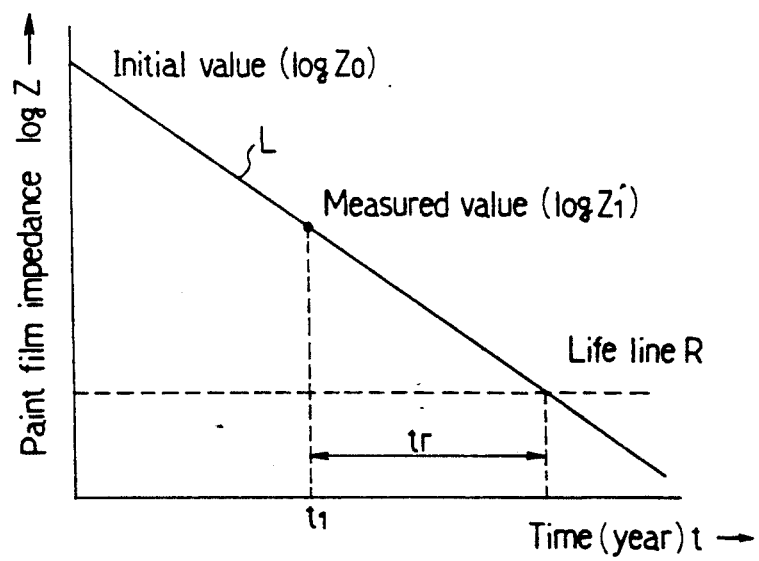
FIG. 2 is a graph showing an assumed life line of the paint film.

FIG. 3 shows an example of the voltage waveform composed so that the power spectrum P becomes $P=1/f$. The phase of each frequency component composing the voltage waveform is randomized so that a peak voltage is suppressed to the utmost. The inventors have found that the logarithm log Z of the paint film impedance has a linearity relative to time t when the measurement frequency ranges from 0.01 Hz to 1 Hz, as is shown in FIG. 2. An analysis of degree of the paint film deterioration can be carried out with ease and accuracy when log Z has the linearity relative to time t, as will be described later. The range of the power spectrum P is determined to be between $P=1/\sqrt{f}$ to $P=1/f^2$ for the following reason. That is, it is desirable that an amount of a low-frequency component should be increased with an amount of a high-frequency component decreased from the point of view that the magnitude of the measured current is increased but it is undesirable that the amount of the high-frequency component should be excessively decreased from the point of view that error of measurement is reduced, as described in detail in Japanese Laid-open (kokai) Patent Application No. 62-102148 (1987) applied for patent by the assignee of the present application. Consequently, the current or the paint film impedance can be measured with high accuracy when the voltage waveform is determined such that the power spectrum P as described above is obtained.

Figure 5:
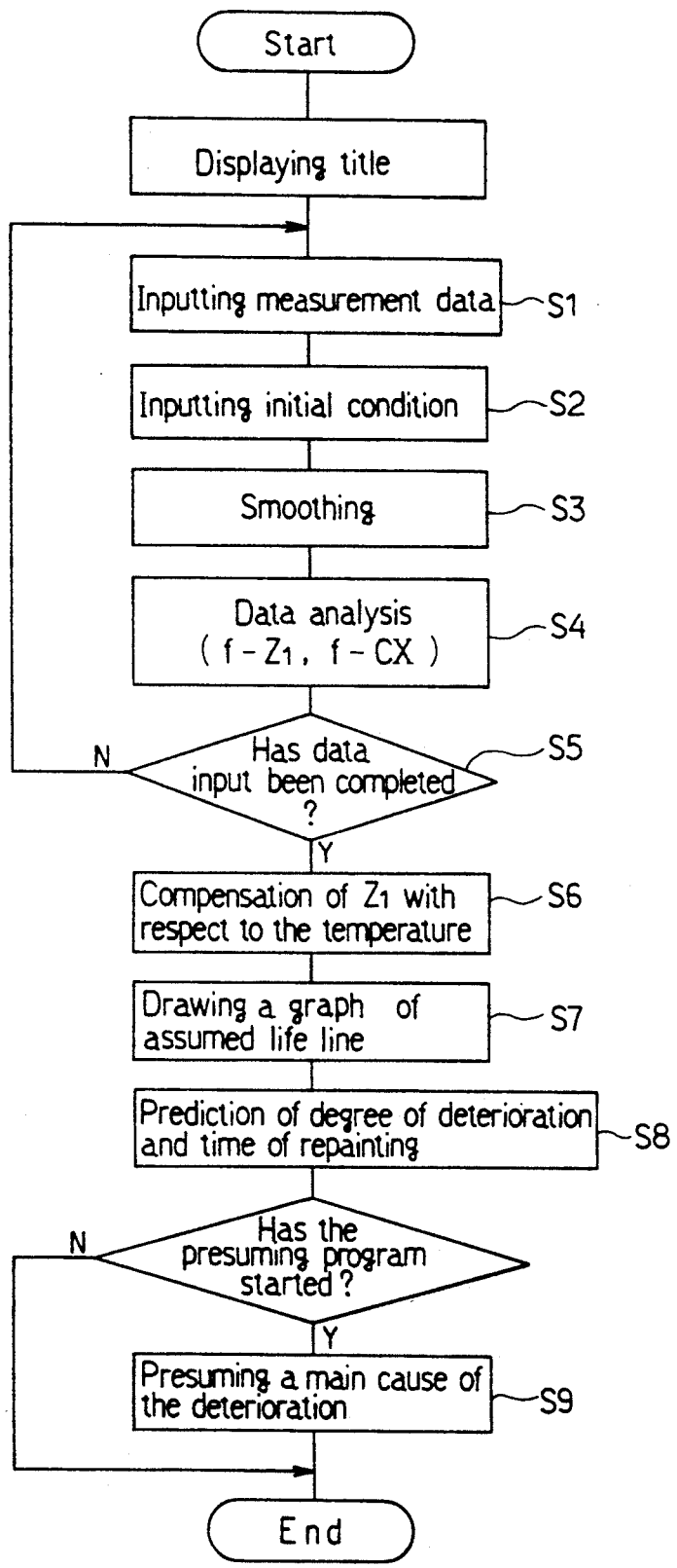
FIG. 5 is a flowchart explaining a procedure of diagnosis in accordance with a diagnosis program.

Upon completion of the measurement of the current or paint film impedance with the probe 10 as described above, the personal computer 1 inputs data of a diagnosis program from the floppy disc 5a and carries out the diagnosis program. A procedure of the diagnosis program will be described with reference to a flowchart of FIG. 5.

Step S1: input of data obtained from measurement:

Measurement data is read out from the floppy disc 5a and the data of the temperature T of the paint film 9 at the time of the impedance measurement, the thickness thereof, the area of the probe 10 in contact with the paint film surface and the like is displayed on the display 6 for confirmation. Subsequently, upon an operation of confirmation, the display 6 is in the initial condition input mode.

Step S2: initial condition input:

Codes representative of the kind of paint of the paint film, the number of elapsing years after formation of the paint film, state of appearance, environment of the equipment on which the paint film is formed, and the like are inputted at the keyboard 7 of the personal computer 1. Three selective elements, that is, the phthalic acid system, the epoxy-urethane system and the others, are provided as the kinds of paints. One of them is selected regarding the kind of paint of the paint film.

Step S3: smoothing:

The obtained data of measured impedance is smoothed. Since data of the measured impedances is not always varied uniformly relative to each frequency, the impedance data is smoothed for improvement of the measurement accuracy.

Step S4: Data analysis:

The value of paint film impedance $Z_1$ at the frequency of 0.1 Hz is obtained based on the smoothed impedance data. For confirmation of suitability of measurement conditions, a graph representing the paint film impedance $Z_1$ and the capacity component Cx is constructed and displayed.

In this case, the paint film impedance Z is considered to be equivalent to a circuit comprising a parallel circuit of a resistance and a capacitor. An amount of resistance component is infinitely increased when the paint film 9 is in the normal condition. Since the amount of resistance component is decreased with deterioration of the paint film 9, the impedance Z is reduced particularly in the low frequency range. Accordingly, the condition of deterioration of the paint film 9 can be roughly comprehended from the above-mentioned graph.

The condition of corrosion of the base metal 11 can also be determined from the graph of the relation between the frequency f and the capacity component Cx. More specifically, the capacity component Cx takes a fixed value relative to the frequency f when the paint film is in the normal condition. However, the capacity of a so-called electrical double layer is increased when the base metal corrodes.

Step S5: repetition of data analysis and determination of abnormal data:

Since the measurement of the paint film impedance $Z_1$ is carried out on a plurality of measurement portions on the surface of an equipment, the above-described data analysis is repeated by the number of the measurement portions. The mean value and dispersion of the values of the paint film impedance $Z_1$ at the frequency of 0.1 Hz at the respective measurement portions are calculated. Abnormal data is eliminated by the t-distribution method as resulting from failures in measurement.

Step S6: compensation of the paint film impedance $Z_1$ with respect to the temperature:

The value of the detected impedance $Z_1$ is varied to a large extent depending upon the temperature of the paint film at the time of measurement. Therefore, the mean value of the impedance $Z_1$ is multiplied by a temperature compensation factor k such that the mean value of the impedance $Z_1$ is converted to the paint film impedance $Z_1'$ at a reference temperature of 25° C., for example.

Figure 8:
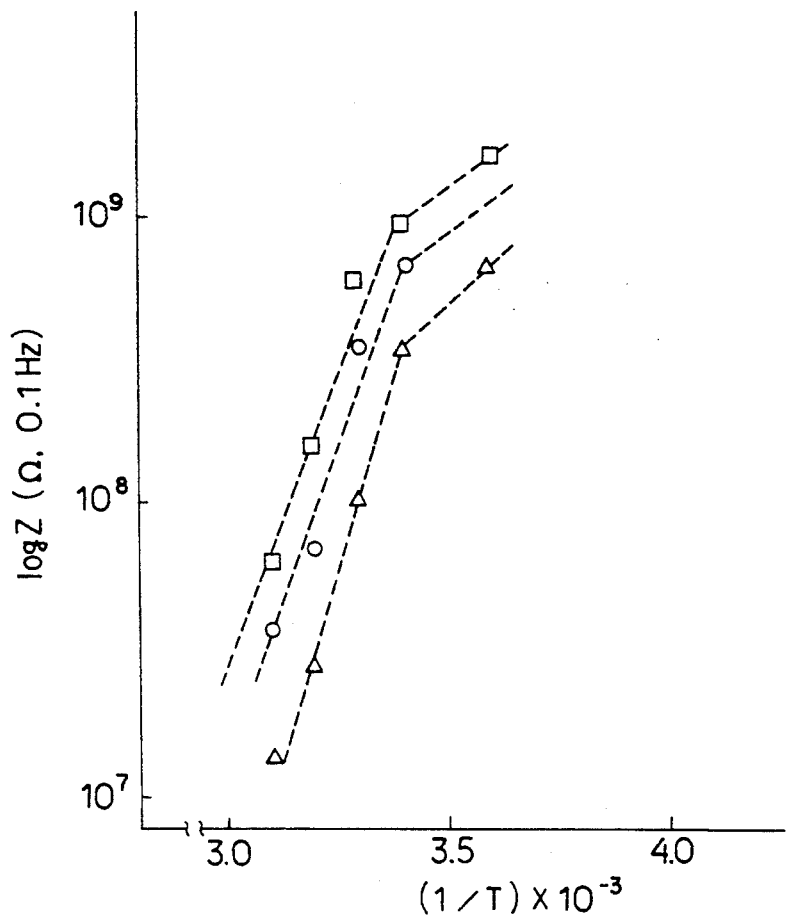
FIG. 8 is a graph of measured data showing the relation between the film impedance and the temperature.

FIG. 8 shows measured data representing the relationship between the inverse numbers of the temperatures T (°K.) of three kinds of paint films 9 and the logarithm log Z of the impedance Z. As understood from FIG. 8, the value of log Z is varied depending upon the temperature T and the variation of log Z is represented as two continuous straight lines having inclinations different from each other with the value of about 25° C. (about 298° K.) as the transition point. Accordingly, the reference temperature is established as 25° C. and the value of impedance $Z_1$ obtained at the temperature T is compensated for as the impedance value at the reference value, 25° C.

Figure 7:
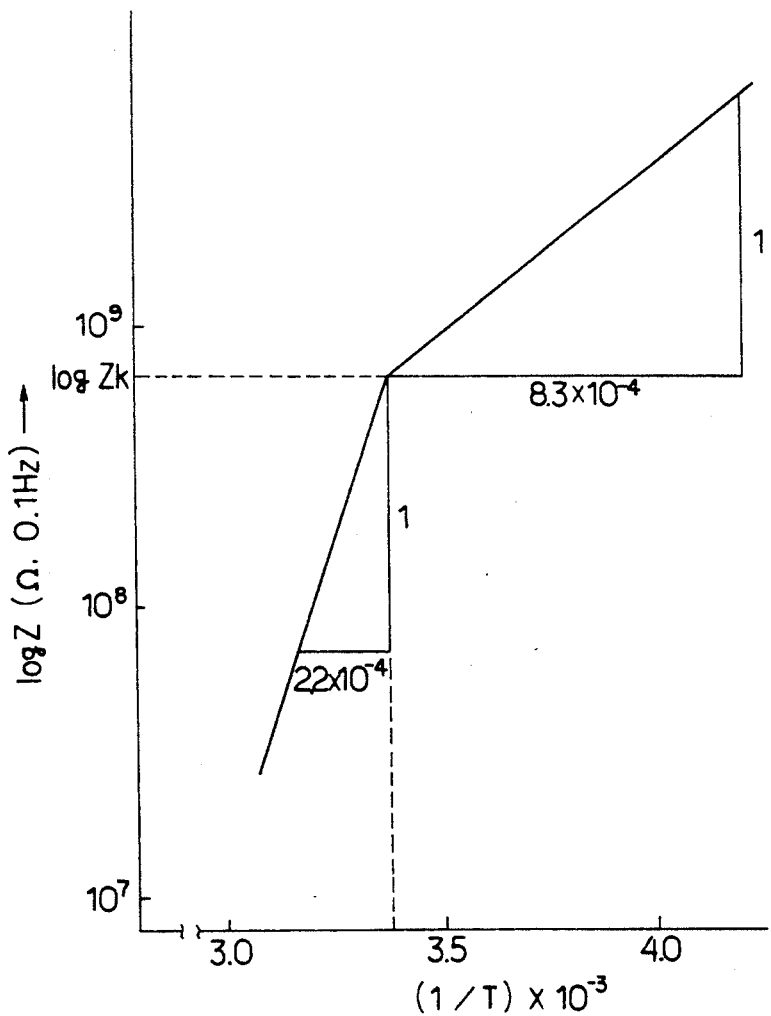
FIG. 7 is a graph showing a relation between the paint film impedance and the temperature.

Now, the temperature compensation factor k is obtained as follows when the paint film 9 the paint material data of which is inputted at step S2 has the relationship shown in FIG. 7. That is, when the temperature is below 25° C., the value of log Z is obtained by the following equation:

$$\log Z = \log Zk + \frac{1}{8.3 \times 10^{-4}} \left( \frac{1}{T} - \frac{1}{298} \right)$$

where Zk = impedance at 25° C. (298° K.)

Similarly, when the temperature is 25° C. or above, the value of log Z is obtained by the following equation:

$$\log Z = \log Zk + \frac{1}{2.2 \times 10^{-4}} \left( \frac{1}{T} - \frac{1}{298} \right)$$

Since the temperature compensation factor k is represented as k = Zk/Z, the factor k is obtained from the above-described equation when the temperature T is below 298° K. (25° C.):

$$k = \exp\left\{ \frac{\log_e 10}{8.3 \times 10^{-4}} \left( \frac{1}{298} - \frac{1}{T} \right) \right\}$$

In the same way, the factor k is obtained as follows when the temperature T is 298° K. (25° C.) or above:

$$k = \exp\left\{ \frac{\log_e 10}{2.2 \times 10^{-4}} \left( \frac{1}{298} - \frac{1}{T} \right) \right\}$$

Figure 6:
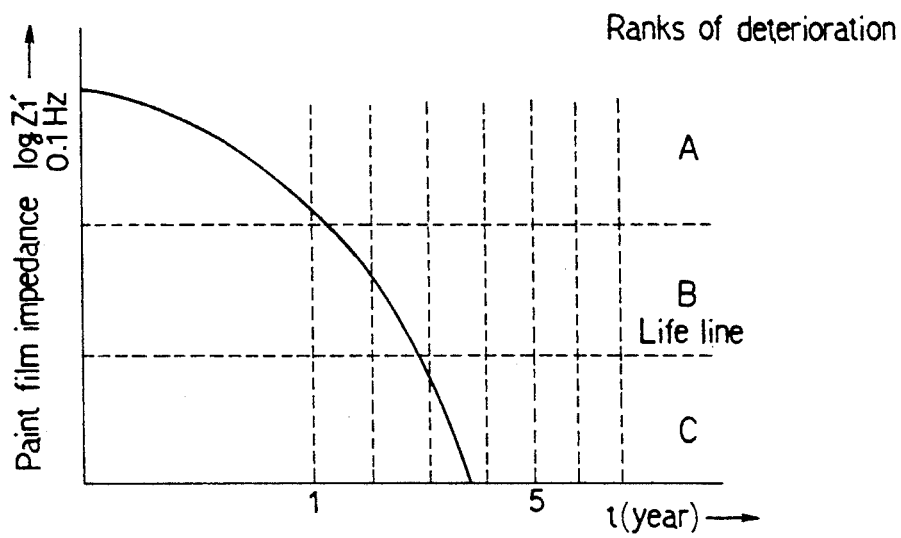
FIG. 6 is a graph showing another example of the assumed life line of the paint film.

Step 7: drawing a diagram of an assumed life line:

As described above, the logarithm log Z of the paint film impedance Z has a linearity relative to the time t. An initial impedance $Z_0$ under the condition that the reference temperature is below 25° C. with respect to the kind of paint whose data has been inputted at step S2 is stored as known data. The data of the number of elapsing years after formation of the paint film has also been inputted at step S2. Based on these data, the assumed life line diagram can be drawn by linking by the straight line L the logarithm log $Z_0$ of the initial impedance $Z_0$ to logarithm log $Z_1'$ of the paint film impedance reduced below the reference temperature on the basis of the detected paint film impedance $Z_1$. The life expectancy tr in FIG. 2 refers to a period of time represented by a section from the time of measurement to the point at which a line extended from the straight line L. The life line R can be previously determined based on degree of the paint film deterioration, degree of rusting on the base metal and the paint film impedance after an exposure test or accelerating test is carried out for the paint film. In the assumed life line graph, an axis of abscissa may be represented by t squared in consideration of the assuming accuracy, as shown in FIG. 6.

The above-described straight line L is obtained by a microcomputer having a program of a functional expression corresponding to an orthogonal graph by finding an equation of a line passing through the initial impedance $Z_0$ and a measured impedance $Z_1$. When a predetermined life-end-point impedance of the paint film is substituted into the equation, the point of intersection between two lines R and L is obtained.

Step S8: prediction of degree of deterioration and the time of repainting:

The degree of deterioration is ranked depending upon what range the value of the paint film impedance $Z_1'$ compensated for with respect to the temperature belongs to. In the embodiment, the paint film deterioration is classified into three ranks A, B and C and information such as shown in FIG. 4 is on the display 6, for example. When the paint film is determined to be at the rank B, the number of years until repainting (remaining life tr) obtained from the above-described assumed life line is displayed.

Step S9: presuming a main cause of the deterioration:

Subsequently, when the personal computer 1 is operated so that a presuming program starts, an expert inference is carried out in an interactive mode so that a main cause of paint film deterioration is inferred based on the result of the measured paint film impedance $Z_1'$. In this program, information about condition of environment of the measured equipment is inputted to the personal computer 1. The result of the inference is displayed on the display 6. The analyzing program is completed after completion of the expert inference or when the deterioration cause presuming program is not started. The result of the deterioration diagnosis and the graph in the midst of analysis can be printed out.

CPU 2 operated in accordance with the above-described diagnosis program thus serves as determination means for performing an analyzing job based on the data of the paint film impedance Z and determining degree of deterioration of the paint film. The result of determination is displayed on the display 6. Consequently, a proper determination can be made about the degree of the paint film deterioration no matter who may operate the diagnosis device. Furthermore, the determination of the paint film deterioration can be performed with ease and accuracy.

The degree of deterioration of the paint film is determined based on the paint film impedance $Z_1'$ obtained by reducing the detected paint film impedance $Z_1$ to the value corresponding to the temperature value below the reference temperature. Consequently, even when the impedance of the paint film is varied by the temperature thereof, an exact determination of the degree of the paint film deterioration can be made.

Figure 9:
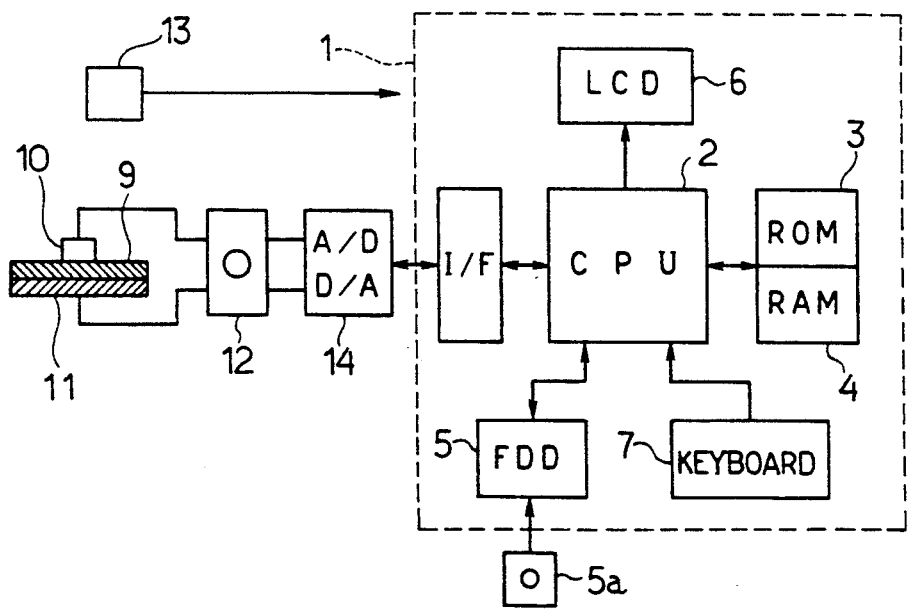
FIG. 9 is a view similar to FIG. 1 illustrating a modified form of the paint film deterioration diagnosis device.

Although the obtained determination is displayed on the display 6 in the foregoing embodiment, it may be printed out by a printer connected to the personal computer 1. Although the personal computer 1 employed in the foregoing embodiment is a general purpose computer, a dedicated purpose personal computer incorporating a display and a printer may be employed. The I/F board 8 attached to the personal computer 1 may or may not be provided with the D/A and A/D functions. Furthermore, circuitry 14 for the A/D conversion and D/A conversion may be externally provided, as is shown as a modified form in FIG. 9.

In the foregoing embodiment, the temperature of the paint film is sensed together with the measurement of the paint film impedance so that the sensed temperature is employed as an element for determination of the degree of the paint film deterioration. Such a temperature sensing means may be provided if necessary.

The foregoing disclosure and drawings are merely illustrative of the principles of the present invention and are not to be interpreted in a limiting sense. The only limitation is to be determined from the scope of the appended claims.

We claim:

1. A method of diagnosing the degree of deterioration of a paint film based on an impedance comprising the steps of:
   a) measuring an impedance by applying a probe to the surface of the paint film, applying voltage across the probe and a base metal on which the paint film is formed, and measuring the resulting current based upon the applied voltage across the probe;
   b) converting an analog signal indicative of the measured current to a corresponding digital impedance signal;
   c) providing a microcomputer with an operational program representative of a functional expression corresponding to an orthogonal graph having an axis representative of the impedance and an axis representative of an elapsed service time period in the year;
   d) inputting to the microcomputer digital data of an initial impedance of the paint film measured at the time of formation of the paint film, the digital impedance signal, an elapsed time period from the time of formation of the paint film until the measurement of the paint film, and a predetermined life-end-point impedance of the paint film;
   e) performing an operation for obtaining an equation representative of a line passing through the initial impedance and the measured impedance on said orthogonal graph;
   f) performing an operation for obtaining in the microcomputer a life end point of the paint film by substituting the predetermined life-end-point impedance into the equation representative of the line passing through the initial impedance and the measured impedance;
   g) obtaining, in the microcomputer a remaining life-duration of the paint film from the time of measurement of the impedance of the paint film to the life end point; and
   h) displaying the obtained remaining life-duration of the paint film on a display.

2. A method according to claim 1, wherein the program representative of the functional expression includes means for converting an impedance value to a logarithmic value.

3. A method according to claim 1, wherein the voltage applied across the probe and the base metal has a plurality of different frequencies.

4. A method according to claim 1, wherein the measured impedance of the paint film is compensated for according to the temperature of the paint film at the time of measurement of the impedance thereof by using the following equation and employing the compensated value $(Z_k)$ for the measured impedance:

$$\log Z_k = \log Z - \frac{1}{\alpha}\left(\frac{1}{T} - \frac{1}{298}\right)$$

where Z is the measured impedance, $\alpha$ is a temperature compensation factor, and T is an absolute temperature (°K.).

5. Apparatus for diagnosing the degree of deterioration of a paint film based on an impedance comprising:
   a) means for measuring an impedance by applying a probe to the surface of the paint film, applying voltage across the probe and a base metal on which the paint film is formed, and measuring the resulting current based upon the applied voltage across the probe;
   b) means for converting an analog signal indicative of the measured current to a corresponding digital impedance signal;
   c) means for providing a microcomputer with an operational program representative of a functional expression corresponding to an orthogonal graph having an axis representative of the impedance and an axis representative of an elapsed service time period in the year;

d) means for inputting to the microcomputer digital data of an initial impedance of the paint film measured at the time of formation of the paint film, the digital impedance signal, an elapsed time period from the time of formation of the paint film until the measurement of the paint film, and a predetermined life-end-point impedance of the paint film;

e) means for performing an operation for obtaining an equation representative of a line passing through the initial impedance and the measured impedance on said orthogonal graph;

f) means for performing an operation for obtaining, in the microcomputer a life end point of the paint film by substituting the predetermined life-end-point impedance into the equation representative of the line passing through the initial impedance and the measured impedance;

g) means for obtaining, in the microcomputer a remaining life-duration of the paint film from the time of measurement of the impedance of the paint film to the life end point; and h) means for displaying the obtained remaining life-duration of the paint film on a display.

* * * * *